United States Patent
Schmidt et al.

(10) Patent No.: US 7,411,103 B2
(45) Date of Patent: Aug. 12, 2008

(54) PROCESS FOR THE CATALYTIC ISOMERISATION OF AROMATIC COMPOUNDS

(75) Inventors: Ivar Schmidt, Copenhagen Ø (DK); Christina Hviid Christensen, Lynge (DK); Michael Brorson, Holte (DK); Erik G. Derouane, Luz-LGS (PT); Claus Hviid Christensen, Lynge (DK); Eric G. Derouane, Luz-LGS (PT)

(73) Assignee: Haldor Topsoe A/S, Lyngby (DK)

( * ) Notice: Subject to any disclaimer, the term of this patent is extended or adjusted under 35 U.S.C. 154(b) by 657 days.

(21) Appl. No.: 10/980,314

(22) Filed: Nov. 4, 2004

(65) Prior Publication Data

US 2005/0113619 A1   May 26, 2005

(30) Foreign Application Priority Data

Nov. 6, 2003   (DK) .................... 2003 01648

(51) Int. Cl.
   *C07C 5/27*   (2006.01)
(52) U.S. Cl. .................................... 585/481
(58) Field of Classification Search ............... 585/481
   See application file for complete search history.

(56) References Cited

U.S. PATENT DOCUMENTS

| | | | |
|---|---|---|---|
| 3,926,782 A | 12/1975 | Plank et al. | |
| 5,098,684 A | 3/1992 | Kresge et al. | |
| 5,495,061 A | 2/1996 | Kulprathipanja | |
| 5,554,274 A * | 9/1996 | Degnan et al. | 208/111.1 |
| 6,565,826 B2 | 5/2003 | Jacobsen et al. | |
| 2001/0024635 A1 | 9/2001 | Beck et al. | |
| 2002/0034471 A1 | 3/2002 | Jacobsen et al. | |

FOREIGN PATENT DOCUMENTS

| WO | WO 00/71255 | 11/2000 |
|---|---|---|
| WO | WO 01/49607 | 7/2001 |

OTHER PUBLICATIONS

N.Y. Chen et al., "Industrial Application of Shape-Selective Catalysis", *Catal. Rev.—Science Engr.*, vol. 28, pp. 185-264 (1988).
K. Tanabe et al., "Industrial Application of Solid Acid-Base Catalysts", *Applied Catalysis A: General*, vol. 181, pp. 399-434 (1999).
C.J.H. Jacobsen et al., "Mesoporous Zeolite Single Crystals," *J. Am. Chem. Soc.*, vol. 122, pp. 7116-7117 (2000).
http://www.uop.com/techsheets/parex.pdf (Information on Parex™ process). (2003).

* cited by examiner

*Primary Examiner*—Thuan Dinh Dang
(74) *Attorney, Agent, or Firm*—Dickstein Shapiro LLP

(57) ABSTRACT

A process for catalytic isomerisation of alkyl aromatic compounds in a hydrocarbon process stream comprising contacting the alkyl aromatic compound-containing hydrocarbon stream under isomerisation conditions with a crystalline zeolite catalyst consisting of individual, primary crystals having an intracrystalline, non-crystallographic mesopore system and a mesopore volume of the zeolite crystals above 0.25.

6 Claims, 1 Drawing Sheet

PROCESS FOR THE CATALYTIC ISOMERISATION OF AROMATIC COMPOUNDS

Figure 1:
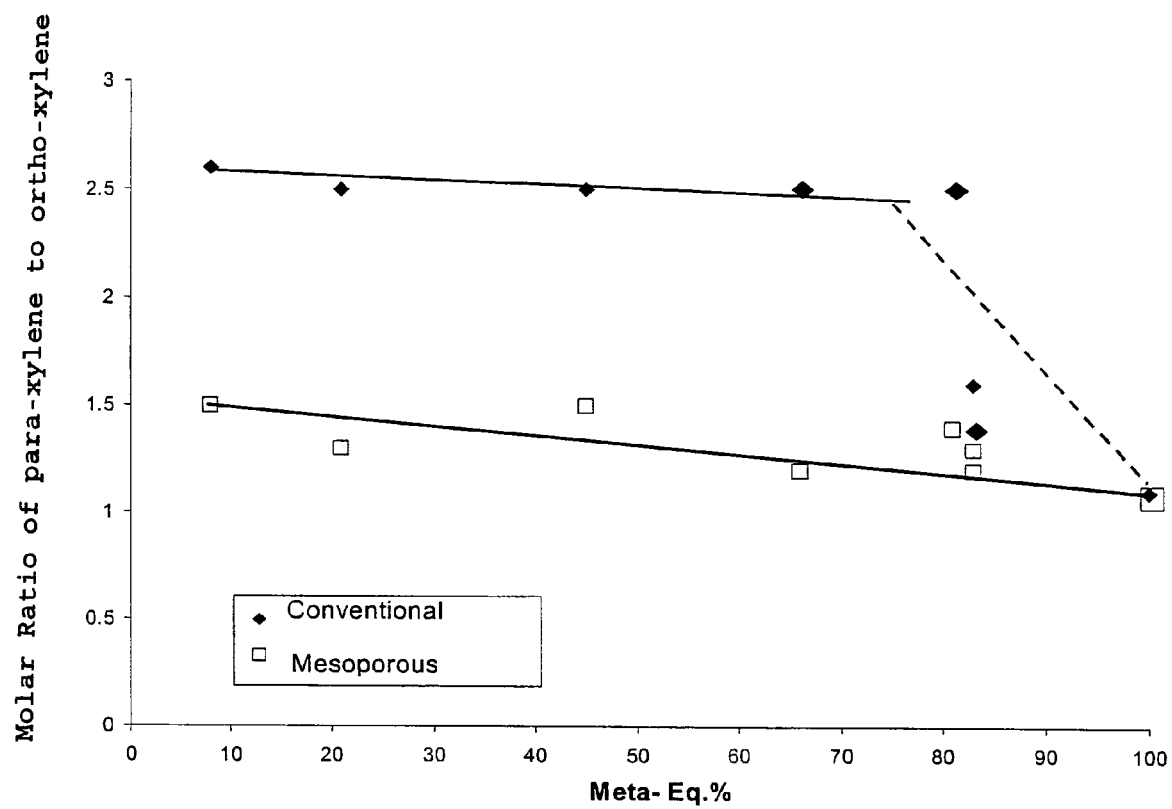

This invention relates generally to the conversion of aromatic hydrocarbons, in particular to the isomerization of a mixture of xylenes using molecular shape selective zeolite catalysts.

Xylene isomerization, which is the conversion of a feed rich in meta-xylene into an equilibrium mixture of the para-isomers, ortho-isomers and meta-isomers in decreasing order of chemical importance, is a major process in the petrochemical industry. Such isomerization is preferentially performed using intermediate pore size molecular shape selective zeolite catalysts, more specifically those derived from ZSM-5 that restrict transalkylation (disproportionation) reactions to undesired trimethylbenzene, toluene and benzene products.

The use of molecular shape selective zeolite catalysts to effect aromatic conversions is well-documented, zeolite ZSM-5 most often being the preferred catalyst. Tuning of the molecular shape selective properties and/or achieving optimal diffusional properties for the transfer of reactants and/or products between the external liquid or gas phase and the zeolite intracrystalline micropores is essential to achieve desired productivity and selectivity. This is described by N.Y. Chen and W. E. Garwood, Catal. Rev.—Sci. Eng., 28 (1986) 185 and by K. Tanabe and W. Hoelderich, Appl. Catal. A: General, 181 (1999) 399. Such tuning modifications include control of pore size by various methods known in the art and/or control of particle size during preparation of the catalyst, but do not include other ways by which access to the zeolite pores can be enhanced without affecting their molecular shape selective properties.

U.S. Pat. No. 2001024635 discloses the preparation of small crystal ZSM-5 and its beneficial use in hydrocarbon conversion reactions such as the disproportionation of toluene and the isomerization of xylenes, where high activity and/or rapid diffusion of the reactants and/or products out of the zeolite pores is/are important. Such ZSM-5 crystals have a crystal size typically less than 0.05 micrometer and their agglomerates have an external surface area greater than 45 $m^2/g$. Packing/agglomeration of nanosized crystals with a particle size distribution in this range results in an intercrystalline porosity with diameters in the mesopore region.

Small zeolite crystals are known in the art to be more prone to deactivation during their catalytic use for hydrocarbon conversions due to faster collapse of their structure as disclosed by W. Zhang, X. Han, X. Liu, X. Bao, Microporous Mesoporous Materials, 50 (2001) 13.

Among the xylenes, the para-isomers and ortho-isomers, the former being highly preferred, are the most desirable compounds and much attention has been devoted to the isomerization of meta-xylene (containing lower amounts of ortho-xylene) to an equilibrium mixture of all three isomers from which the para-isomer can be separated by either adsorption or crystallization.

The adsorption process is further described in U.S. Pat. No. 5,495,061. Information on this process, also known as the Parex™ Process, is also described on the following Internet website http://www.uop.com/techsheets/parex.pdf.

The crystallisation process is described by T. C. Tsai, S. B. Liu, I. Wang, Applied Catalysis A: General, 181 (1999) 355. The equilibrium mixture consists of approximately 50% meta-xylene and equal amounts of para-xylenes and ortho-xylenes. However, both meta-xylenes and ortho-xylenes are more bulky than para-xylene, which results in diffusional limitations for their access to the zeolite catalyst micropores. Therefore, small zeolite crystal catalysts are preferred.

WO patent applications Nos. 00/71255 and 01/49607 describe other types of mesoporous materials known as catalysts for isomerisation of alkyl aromatics. These mesoporous catalysts have the disadvantage of not being true crystalline materials. They have a lower thermal stability and lower acid strength. In addition, they are not effective against carbon deposition. An example of these types of materials is the MCM-41 materials, which are further described in U.S. Pat. No. 5,098,684.

U.S. Pat. No. 3,926,782 discloses hydrocarbon conversions over ZSM-5 crystals having a crystal size of 0.005-0.1 micrometer and U.S. Patent Application No. 2001024635 discloses small crystal ZSM-5 with a size less than about 0.05 micrometer as a useful and improved catalyst for the liquid phase isomerization of xylene. The latter catalyst is an agglomerate of small ZSM-5 crystals with intercrystalline mesopores and having an external surface area greater than 45 $m^2/g$, allowing easier access of meta-xylene and ortho-xylene to the micropores of the zeolite and demonstrating higher activity at lower isomerisation conversion temperature (40° C.). However, it is known in the art that smaller zeolite crystals have less intrinsic stability as disclosed by W. Zhang, X. Han, X. Liu, X. Bao, Micropor.Mesopor.Mater., 50 (2001) 13.

U.S. Pat. No. 6,565,826 and U.S. Patent Application No. 20020034471, both of which are incorporated herein by reference, disclose the preparation of large zeolite primary crystals possessing determined and tuneable intracrystalline mesopore systems, tortuous or straight, respectively. ZSM-5 crystals prepared according to the disclosed processes have sizes typically exceeding 0.5 micrometer in two directions and a mesopore volume greater than 0.25 mL/g. Compared to conventional zeolite crystals of comparable size, these mesoporous zeolite crystals exhibit significantly improved diffusional properties. This is further described by C. J. H. Jacobsen, J. Houzvicka, I. Schmidt, A. Carlsson, J. Am. Chem. Soc., 122 (2000) 7116, incorporated herein by reference.

There is, therefore, a need to synthesize and use zeolite catalysts whose crystal properties enable enhanced access to their intracrystalline micropores whilst preserving their structural framework stability.

This invention concerns a process for the conversion of aromatic hydrocarbons, in particular for the isomerization of a mixture of xylenes, containing predominantly the meta-xylene isomer, into an equilibrium mixture of xylene isomers enriched in para-xylenes and ortho-xylenes using molecular shape selective zeolite catalysts restricting transalkylation (disproportionation) reactions. Transalkylation would otherwise result in the formation of undesired trimethylbenzenes and toluene. More specifically, this invention relates to the high performance of such molecular shape selective zeolites whose crystals possess structural mesopores within the individual zeolite crystals in addition to their framework micropores.

BRIEF DESCRIPTION OF THE SEVERAL VIEWS OF THE DRAWING(S)

FIG. 1 which is a plot of the para-xylene/ortho-xylene ratio as a function of the approach to equilibrium represented by m-X Eq. % (amount of meta-xylene converted relative to the maximum possible amount of meta-xylene converted when full equilibrium is reached).

It has now been found that crystalline zeolites with a mesoporous structure as described in U.S. Pat. No. 6,565,826 and U.S. Patent Application No. 20020034471 have improved activity for the conversion of alkylated aromatic compounds, more specifically the isomerization of meta-xylene and thus also, as known in the art, for other related aromatic hydrocarbon conversion reactions such as the disproportionation of toluene.

A process for the selective conversion of aromatic hydrocarbons, such as the conversion of the meta-xylene and ortho-xylene isomers, to an equilibrium mixture of the xylenes isomers in the presence of a mesoporous zeolite in particular mesoporous ZSM-5, is described. This mesoporous zeolite has large zeolite primary crystals with intracrystalline mesopores obtained by crystallization of the zeolite within and on the surface of a matrix that can be removed after synthesis.

These mesoporous zeolites show superior properties for the conversion of hydrocarbon feedstocks containing aromatic compounds, preferentially xylene isomerization and toluene disproportionation, and more preferentially xylene isomerization.

Accordingly, the invention concerns a process for catalytic isomerisation of alkyl aromatic hydrocarbons in a hydrocarbon process stream comprising contacting the alkyl aromatic compound-containing hydrocarbon stream under isomerisation conditions with a crystalline zeolite catalyst consisting of individual, primary crystals having an intracrystalline, non-crystallographic mesopore system and a mesopore volume of the zeolite crystals above 0.25 ml/g.

The terms mesoporous and mesopore(s) as used herein refer to mesoporous zeolites consisting of individual, primary crystals having an intracrystalline, non-crystallographic mesopore system and a mesopore volume of the zeolite crystals above 0.25 ml/g and containing mesopores within each crystal having a pore size range according to the IUPAC definition of mesopores, i.e. a pore diameter in the range 2-50 nanometer.

The mesoporous crystals have been found to be useful as catalysts in aromatic hydrocarbon conversion reactions where high activity and/or rapid diffusion of the reactants and/or products out of the zeolite catalyst micropores are important. These criteria are also important in for example the hydroisomerization of paraffins as described by J. Houzvicka, C. J. H. Jacobsen, I. Schmidt, Stud. Surf. Sci. Catal., 135 (2001) 158.

These mesoporous zeolite catalysts have the advantage in alkyl aromatic isomerisation of being effective in preventing carbon deposition and having a large number of easily accessible active sites. They have the advantage of having an improved thermal stability and higher acid strength than the MCM-41 type materials.

The mesoporous zeolite catalyst is exemplified by mesoporous ZSM-5 and the alkyl aromatic compound is exemplified by the xylene.

Mesoporous ZSM-5 is normally synthesized as an aluminosilicate. However, the framework aluminium can be partially or completely replaced by other trivalent elements, such as boron, iron and/or gallium and the framework silicon by other tetravalent elements such as germanium or titanium.

The mesoporous ZSM-5 crystals applicable in the invention as catalysts have sizes typically exceeding 0.5 micrometer in two directions as measured by transmission (TEM) or scanning (SEM) electron microscopy.

The acidic, monofunctional, mesoporous ZSM-5 crystals can be converted into bifunctional catalysts by the addition of hydrogenation/dehydrogenation function, usually a group VIII metal, in particular platinum.

When used as catalysts, it may be desirable to incorporate the large mesoporous zeolite with one or more other materials resistant to the temperatures and other conditions employed in the processes for which they are used. Such materials include active or inactive, natural or synthetic, porous or non-porous materials with the zeolite content ranging from 1 to about 90% by weight.

The isomerization of xylenes can be operated under conditions including a temperature about 200-600° C., a pressure of from about 1-100 atmospheres (100-10,000 kPa), a weight hourly space velocity (WHSV) of from about 0.5 to 100 $h^{-1}$ and a hydrogen/hydrocarbon mole ratio of 0-10 to about 10 [N. Y. Chen, W. E. Garwood, Catal. Rev.-Sci. Eng., 28 (1986) 185].

Low-pressure xylene isomerization is an example of a process, where no hydrogen is applied and where the isomerization reaction using a catalyst of relatively high acidity in the temperature range from about 300° C. to 400° C., is generally the second stage of a two-stage process in which the $C_8$ aromatic stream is initially subjected to an ethylbenzene conversion step. High-temperature xylene isomerization uses a ZSM-5 catalyst of low acidity containing trace concentrations of platinum, operating at temperatures above 425° C. enabling the hydrodealkylation of ethylbenzene.

The invention and the manner of practicing the same are more fully illustrated in the following examples.

EXAMPLES

Example 1 (Comparative Example)

Preparation of Conventional ZSM-5

A conventional ZSM-5 zeolite was prepared by crystallization of a gel with the molar composition1 $Al_2O_3$: 9 $TPA_2O$: 1.25 $Na_2O$: 50 $SiO_2$: 385 $H_2O$. The gel was obtained by adding an aqueous solution of tetrapropylammonium hydroxide (147 g, 40 wt %) to the water (22 g) and subsequently adding sodiumaluminate (3.00 g, $NaAlO_2$, 54 wt % $Al_2O_3$, 41 wt % $Na_2O$) to the mixture while stirring. Stirring was continued until the sodiumaluminate was dissolved followed by the addition of tetraethylorthosilicate (166 g, $Si(OCH_2CH_3)_4$, 99%).

The obtained two-phase system was stirred vigorously for 3 hours during this period the tetraethylorthosilicate is hydrolyzed resulting in a single aqueous phase gel. The gel was introduced into a teflon-lined stainless steel autoclave and heated to 180° C. for 72 h. After cooling the autoclave to room-temperature, the product was suspended in water, filtered by suction, resuspended in water and filtered again. This procedure was repeated four times.

Finally, the product was dried at 110° C. for 10 h. The dried product was calcined in a muffle furnace at 550° C. for 4 h. Subsequently, the calcined zeolite was ion-exchanged using 10 g of a 2 M $NH_4NO_3$ solution per g of zeolite. The suspension was heated to 60° C. for 2 hours, while stirring and the zeolite was separated from the ion-exchange solution by filtering and the ion-exchange was repeated. Then the suspension was filtered and the filter cake was washed with distilled water, dried at 110° C. for 10 h followed by calcination in a muffle furnace at 550° C. for 4 h to obtain the zeolite on $H^+$-form.

The resultant H-ZSM-5 catalyst had a silica/alumina ($SiO_2/Al_2O_3$) molar ratio of 50 determined by atomic emission spectroscopy (AES), a BET surface area of 370 $m^2/g$ measured by nitrogen adsorption and an average crystal size of 0.2 micrometer as estimated from SEM measurements. The acidity of the catalyst was measured by ammonia adsorption and temperature programmed desorption and the concentration in acid sites was estimated to be 0.094 mmol/g.

Example 2

Preparation of Mesoporous ZSM-5

A mesoporous ZSM-5 zeolite was prepared by drying 40 g of carbon black (Black Pearls 2000 supplied by Carbot Corp.) at 130° C. for 12 hours. The cooled carbon black was impregnated with a clear solution of tetrapropylammonium hydroxide (40 wt %, 73.5 g), sodium aluminate (NaAlO$_2$, 54 wt % Al$_2$O$_3$, 41 wt % Na$_2$O, 0.75 g), water (11 g) and ethanol (65 g). After evaporation of the ethanol, the carbon black was impregnated with the corresponding amount tetraethylorthosilicate (99%, Si(OCH$_2$CH$_3$)$_4$, 83 g) resulting in a incipient wetness impregnation of the carbon black. The composition of the resulting synthesis gel was 1 Al$_2$O$_3$:20 TPA$_2$O:1 Na$_2$O: 100 SiO$_2$:200H$_2$O:200 EtOH.

After aging for 12 hours at room-temperature, the impregnated carbon black was introduced into a stainless steel autoclave containing a sufficient amount of water to produce saturated steam and heated to 180° C. for 72 hours. After cooling the autoclave to room-temperature, the product was suspended in water, filtered by suction, resuspended in water and filtered again. This procedure was repeated four times.

Then the product was dried at 110° C. for 10 hours. The carbon black matrix was removed by combustion in a muffle furnace at 550° C. for 8 hours. Subsequently, the calcined zeolite was ion-exchanged using 10 g of a 2 M NH$_4$NO$_3$ solution per g of calcined zeolite. The suspension was heated to 60° C. for 2 hours while stirring and the zeolite was separated from the ion-exchange solution by filtering and the ion-exchange was repeated. Then the suspension was filtered and the filter cake was washed with distilled water, dried at 110° C. for 10 hours followed by calcination in a muffle furnace at 550° C. for 4 h to obtain the zeolite on H$^+$-form.

The resultant mesoporous H-ZSM-5 catalyst had a silica/alumina (SiO$_2$/Al$_2$O$_3$) molar ratio of 110 determined by atomic emission spectroscopy (AES), a BET surface area of 350 m$^2$/g and a mesoporous volume of 0.4 cc/g, both measured by nitrogen adsorption and an average crystal size of 1.0 micrometer as estimated from SEM measurements. The acidity of the catalyst was measured by ammonia adsorption and temperature programmed desorption and the concentration in acid sites was estimated to be 0.119 mmol/g. The zeolite catalysts of Example 1 and Example 2 have thus acidities that are reasonably similar within experimental error although they largely differ by their crystal size and mesoporous volume.

Example 3

Isomerisation of Meta-Xylene

The H-ZSM-5 catalysts of Example 1 and Example 2 were pelletized, crushed and sized to particles of size in the range 150-300 micrometer and used to effect the isomerization of meta-xylene.

In each case, testing was conducted using a catalytic microreactor unit comprising a glass-lined U tube reactor loaded with 0.17 g of catalyst giving a bed height of about 25 mm. Temperature was varied between 175° C. and 450° C. and pressure between 1.0 and 12.7 atmosphere. Liquid meta-xylene was added to a preheated He carrier gas flowed through the reactor, the meta-xylene/helium molar ratio being 1/20 at low pressures and 1/5 at high pressures. Meta-xylene WHSVs were 3 h$^{-1}$ and 6 h$^{-1}$, respectively. Products were analyzed on-line by gas chromatography assuming the following response factors (flame ionization detection): benzene=1.12, toluene=1.07, xylenes=1.04, 1,2,4-trimethylbenzene=1.02.

Detailed results are tabulated in Table 1. The compositions of the xylenes effluent mixture exiting the reactor for the various runs are listed in Table 2. The approach to equilibrium as a function of conversion is shown in FIG. 1. Results are only reported in the 250-450° C. temperature range. The equilibrium mixture of the xylenes isomers in this temperature range consists of approximately 53% meta-xylene, 25% ortho-xylene and 22% para-xylene.

TABLE 1

| Experimental Conditions | | | Conventional H-ZSM-5 | | | Mesoporous H-ZSM-5 | | |
|---|---|---|---|---|---|---|---|---|
| Pressure (atm) | T (° C.) | WHSV (h$^{-1}$) | meta Con. % | meta Eq. % | Para/ortho ratio | meta Con. % | meta Eq. % | para/ortho ratio |
| 2.4-2.5 | 300 | 3 | 21 | 45 | 2.5 | 29 | 62 | 1.5 |
|  | 350 | 3 | 39 | 83 | 1.6 | 43 | 91 | 1.3 |
|  | 400 | 3 | 47 | ~100 | 1.1 | 47 | ~100 | 1.1 |
| 5.9-6.8 | 300 | 6 | 10 | 21 | 2.5 | 21 | 45 | 1.3 |
|  | 350 | 6 | 39 | 83 | 1.4 | 43 | 92 | 1.2 |
| 8.9-9.9 | 275 | 6 | 4 | 8 | 2.6 | 8 | 17 | 1.5 |
|  | 300 | 6 | 19 | 81 | 2.5 | 31 | 66 | 1.4 |
| 12.6-12.8 | 250 | 6 | 4 | 9 | 4.6 | 29 | 62 | 1.2 |
|  | 300 | 6 | 31 | 66 | 2.5 | 43 | 91 | 1.2 | a. meta Con. %: conversion (%) of meta-xylene.
b. meta Eq. %: approach to equilibrium conversion relative to meta-xylene maximum conversion.
c. para/ortho ratio: para-xylene/ortho-xylene ratio in the products.

The results shown in Table 1 demonstrate that mesoporous H-ZSM-5 enables a higher meta-xylene conversion in all cases and thus equilibrium can be reached at lower temperatures. In particular, the mesoporous H-ZSM-5 catalyst is approximately 20° C. more active than the conventional catalyst in the 5.9-9.9 atmosphere pressure range. By this is meant that similar conversions are obtained at a temperature 20° C. lower (T-20° C.) for the mesoporous zeolite based catalyst compared to the reference. At a pressure of approximately 12.7 atmospheres the mesoporous H-ZSM-5 catalyst is approximately 60° C. more active. The results also show that the para-xylene to ortho-xylene mole ratio is always closer to its equilibrium value, i.e. approximately unity, when using mesoporous ZSM-5 as catalyst (columns 6 and 9). The improved performance of mesoporous H-ZSM-5 catalysts is particularly striking at higher pressure and low temperature, i.e. when diffusional limitations are expected to be more important.

Table 2 shows the composition of the xylenes effluent mixture for various operating conditions.

TABLE 2

| Experimental Conditions | | | Conventional H-ZSM-5 | | | Mesoporous H-ZSM-5 | | |
|---|---|---|---|---|---|---|---|---|
| Pressure (atm) | T (° C.) | WHSV ($h^{-1}$) | meta (%) | ortho (%) | para (%) | meta (%) | ortho (%) | para (%) |
| 2.4-2.5 | 300 | 3 | 79 | 6 | 15 | 69 | 12 | 19 |
|  | 350 | 3 | 61 | 15 | 24 | 57 | 19 | 24 |
|  | 400 | 3 | 53 | 23 | 24 | 53 | 23 | 24 |
| 5.9-6.8 | 300 | 6 | 90 | 3 | 7 | 79 | 9 | 12 |
|  | 350 | 6 | 61 | 16 | 23 | 57 | 20 | 23 |
| 8.9-9.9 | 275 | 6 | 96 | 1 | 3 | 92 | 3 | 5 |
|  | 300 | 6 | 81 | 5 | 14 | 69 | 13 | 18 |
| 12.6-12.8 | 250 | 6 | 96 | 1 | 3 | 71 | 13 | 16 |
|  | 300 | 6 | 69 | 9 | 22 | 57 | 20 | 23 | meta (%): percentage of meta-xylene
ortho (%): percentage of ortho-xylene
para (%): percentage of para-xylene The results shown in Table 2 further demonstrate that the mesoporous H-ZSM-5 catalyst has improved activity for the isomerization of meta-xylene to an equilibrium mixture of the xylenes as seen from the smaller amount of meta-xylene for all temperatures and pressures at which testing was conducted.

The quality of the approach to equilibrium is further demonstrated in FIG. 1 which is a plot of the para-xylene/ortho-xylene ratio as a function of the approach to equilibrium represented by m-X Eq.% (amount of meta-xylene converted relative to the maximum possible amount of meta-xylene converted when full equilibrium is reached):

At conversions below about 80%, the conventional H-ZSM-5 catalyst has the exceptional property of producing para-xylene at selectivities far exceeding the approximate 1:1 para-xylene to ortho-xylene ratio expected from an equilibrium conversion. Reduction in the average micropore length by introducing mesopores in large primary crystals of H-ZSM-5 reduces the selectivity to para-xylene and enables shifting the isomers equilibrium distribution towards the equilibrium composition.

Mesoporous H-ZSM-5 has improved properties relative to conventional H-ZSM-5 for the isomerization of meta-xylene, in particular at lower temperatures which may reduce utility consumptions.

Example 4

The H-ZSM-5 catalysts of Example 1 and Example 2 were pelletized, crushed and sized to particles of size in the range 150-300 micrometer and used to effect the isomerization of meta-xylene as well as converting ethylbenzene present in the feed.

In each case, testing was conducted using a catalytic microreactor unit comprising a glass-lined U tube reactor loaded with 0.17 g of catalyst, giving a bed height of about 25 mm. Temperature was varied between 350° C. and 450° C. at a pressure of 6 atmosphere. A liquid comprising 15 Vol. % ethylbenzene and 85 Vol. % meta-xylene was added to a preheated He carrier gas flowed through the reactor, the aromatics/helium molar ratio being 1/5. Aromatics were ethylbenzene and meta-xylene. WHSV was 6 $h^{-1}$.

Products were analyzed on-line by gas chromatography assuming the following response factors (flame ionization detection): benzene=1.12, toluene=1.07, xylenes=1.04, 1,2,4-trimethylbenzene=1.02, ethylbenzene=1.08.

Detailed results using conventional H-ZSM-5 and mesoporous ZSM-5 are tabulated in Table 3, which shows the conversion of ethylbenzene at xylene isomerization operating conditions.

TABLE 3

| Temp (° C.) | Conventional H-ZSM-5 Ethylbenzene Conversion (%) | Mesoporous H-ZSM-5 Ethylbenzene Conversion (%) |
|---|---|---|
| 350 | 22.4 | 44.7 |
| 400 | 51.3 | 68.4 |
| 450 | 80.1 | 83.8 |

The results in Table 3 demonstrates that mesoporous H-ZSM-5 is very capable of converting ethylbenzene at xylene isomerization conditions and thereby avoiding accumulation of ethylbenzene in the separation isomerization loop.

The invention claimed is:

1. A process for catalytic isomerisation of alkyl aromatic hydrocarbons in a hydrocarbon process stream comprising:
   contacting the alkyl aromatic compound-containing hydrocarbon stream under catalytic isomerisation conditions with a crystalline zeolite catalyst consisting of individual, primary crystals having an intracrystalline, non-crystallographic mesopore system and a mesopore volume of the zeolite crystals above 0.25 cc/g; and
   effecting isomerisation of the alkyl aromatic hydrocarbons.

2. A process according to claim 1, wherein the hydrocarbon process stream comprises $C_8$ aromatic compounds.

3. A process according to claim 2, wherein the $C_8$ aromatic compounds are a mixture of xylene isomers.

4. A process according to claim 3, wherein the xylene isomer is meta-xylene.

5. A process according to claim 1, wherein the zeolite catalyst is ZSM-5.

6. A process according to claim 1, wherein the crystals of the zeolite catalyst have dimensions of at least 0.5 μm in two directions and a mesopore volume above 0.25 cc/g.

* * * * *